United States Patent
Sato et al.

(10) Patent No.: US 10,820,870 B2
(45) Date of Patent: Nov. 3, 2020

(54) X-RAY DIAGNOSTIC APPARATUS AND X-RAY HIGH-VOLTAGE GENERATOR

(71) Applicant: Canon Medical Systems Corporation, Otawara (JP)

(72) Inventors: Daisuke Sato, Utsunomiya (JP); Katsuo Takahashi, Yaita (JP); Kansei Takahashi, Nasushiobara (JP); Hiroyoshi Kobayashi, Nasushiobara (JP); Akio Tetsuka, Shioya (JP); Akira Mochizuki, Nasushiobara (JP); Katsunori Kojima, Hadano (JP); Yuki Totsuka, Nasushiobara (JP); Masaharu Soya, Nasushiobara (JP); Ikuo Hayashida, Yaita (JP)

(73) Assignee: Canon Medical Systems Corporation, Otawara (JP)

( * ) Notice: Subject to any disclaimer, the term of this patent is extended or adjusted under 35 U.S.C. 154(b) by 0 days.

(21) Appl. No.: 16/144,231

(22) Filed: Sep. 27, 2018

(65) Prior Publication Data

US 2019/0099142 A1   Apr. 4, 2019

(30) Foreign Application Priority Data

Oct. 3, 2017 (JP) .................................. 2017-193580
Sep. 20, 2018 (JP) .................................. 2018-176429

(51) Int. Cl.
*A61B 6/00* (2006.01)
*H01J 35/10* (2006.01)
*H05G 1/66* (2006.01)

(52) U.S. Cl.
CPC .......... *A61B 6/4441* (2013.01); *A61B 6/4452* (2013.01); *A61B 6/54* (2013.01); *H01J 35/10* (2013.01); *H05G 1/66* (2013.01); *A61B 6/586* (2013.01); *H01J 2235/1093* (2013.01)

(58) Field of Classification Search
None
See application file for complete search history.

(56) References Cited

U.S. PATENT DOCUMENTS

2008/0056451 A1 * 3/2008 Gotoh .................. A61B 6/4441
378/197

FOREIGN PATENT DOCUMENTS

JP   2013-182764   9/2013

* cited by examiner

*Primary Examiner* — Hoon K Song
(74) *Attorney, Agent, or Firm* — Oblon, McClelland, Maier & Neustadt, L.L.P.

(57) ABSTRACT

According to one embodiment, an X-ray diagnostic apparatus includes an X-ray tube, a driver, a supporter, and processing circuitry. The X-ray tube including a rotating anode. The driver rotates the rotating anode. The supporter supports the X-ray tube in an inclinable manner. The processing circuitry acquires information indicating an attitude of the supporter and controls the driver based on information indicating the acquired attitude.

17 Claims, 10 Drawing Sheets

| C-arm angle | Anode rotation control data | | Operation sound data | Noise determination |
| --- | --- | --- | --- | --- |
| | Rotation frequency | Voltage waveform | | |
| A | f_1 | v_1 | S_A | OK |
| B | f_1 | v_1 | S_B | NG |
| C | f_1 | v_1 | S_C | OK |
| D | f_1 | v_1 | S_D | OK |
| E | f_1 | v_1 | S_E | OK |
| F | f_1 | v_1 | S_F | OK |
| G | f_1 | v_1 | S_G | NG |

| C-arm angle | Anode rotation control data | | Operation sound data | Noise determination |
|---|---|---|---|---|
| | Rotation frequency | Voltage waveform | | |
| A | f_1 | v_1 | S_A | OK |
| B | f_2 | v_1 | S_B' | OK |
| C | f_1 | v_1 | S_C | OK |
| D | f_1 | v_1 | S_D | OK |
| E | f_1 | v_1 | S_E | OK |
| F | f_1 | v_1 | S_F | OK |
| G | f_3 | v_2 | S_G'' | OK |

X-RAY DIAGNOSTIC APPARATUS AND X-RAY HIGH-VOLTAGE GENERATOR

CROSS-REFERENCE TO RELATED APPLICATIONS

This application is based upon and claims the benefit of priority from Japanese Patent Applications No. 2017-193580, filed Oct. 3, 2017; and No. 2018-176429, filed Sep. 20, 2018; the entire contents of both of which are incorporated herein by reference.

FIELD

Embodiments described herein relate to an X-ray diagnostic apparatus and an X-ray high-voltage generator.

BACKGROUND

A rotating anode type X-ray tube, for example, is known as an X-ray source of an X-ray diagnostic apparatus. A rotating anode type X-ray tube disperses an impact of thermoelectrons over a wide range of a target provided on an anode by rotation of the anode. Thus, such a rotating anode type X-ray tube achieves a larger X-ray output than a fixed anode type X-ray tube.

On the other hand, a rotating anode type X-ray tube may produce noise as a result of resonance in a container that contains the X-ray tube if the rotation frequency of the anode and the resonance frequency of the container match. As a method for suppressing such resonance, a method of braking the anode if the rotation frequency of the anode is close to the resonance frequency of the container is known.

Usually, there is no particular problem with the aforementioned X-ray diagnostic apparatus; however, the inventors have noted that such an apparatus requires improvement in the following respect.

For example, in an X-ray diagnostic apparatus, a supporter that supports an X-ray tube, such as a C-arm, takes various attitudes, according to the status of use. At this time, depending on the attitude of the supporter, the vibration generated at the time of rotation of the anode may cause resonance in the supporter, thus generating noise. However, it is difficult to address such noise, since the attitude of the supporter variously changes.

DETAILED DESCRIPTION

According to one embodiment, an X-ray diagnostic apparatus includes an X-ray tube, a driver, a supporter, and processing circuitry. The X-ray tube including a rotating anode. The driver rotates the rotating anode. The supporter supports the X-ray tube in an inclinable manner. The processing circuitry acquires information indicating an attitude of the supporter and controls the driver based on information indicating the acquired attitude.

Hereinafter, embodiments will be described with reference to the accompanying drawings. The same reference symbols will be used to denote elements similar or corresponding to elements that have been described, and redundant explanations will be omitted. Explanations will be given mainly of elements that have not been described.

Figure 1:
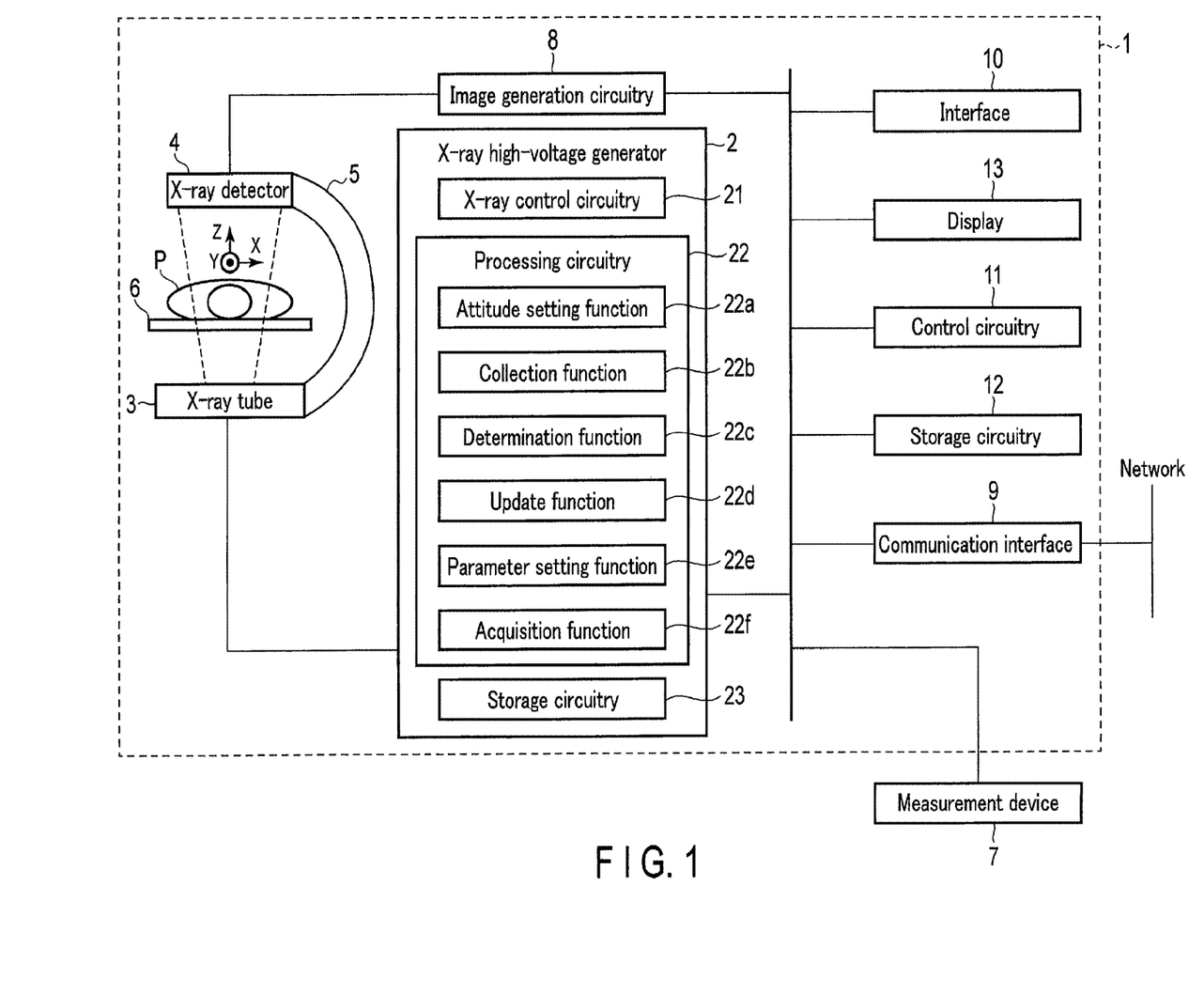
FIG. 1 is a block diagram showing an example of a configuration of an X-ray diagnostic apparatus according to an embodiment.

FIG. 1 is a block diagram showing a configuration example of an X-ray diagnostic apparatus 1 according to an embodiment. The X-ray diagnostic apparatus 1 includes: an X-ray high-voltage generator 2; a bed that includes an X-ray tube 3, an X-ray detector 4, a supporter 5, and a table top 6; a measurement device 7; image generation circuitry 8; a communication interface 9; an interface 10; control circuitry 11; storage circuitry 12; and a display 13. The measurement device 7 may be detached as necessary.

The X-ray diagnostic apparatus 1 corresponds to, for example, a diagnostic apparatus for cardiovascular X-ray fluoroscopy for use in angiographic examinations, etc. The X-ray diagnostic apparatus 1 may be, for example, an X-ray fluoroscopic diagnosis apparatus for use in gastrointestinal series examinations.

The X-ray high-voltage generator 2 includes X-ray control circuitry 21, processing circuitry 22, and storage circuitry 23. The X-ray high-voltage generator 2 generates a tube current to be applied to the X-ray tube 3 and a tube voltage to be applied to the X-ray tube 3. The X-ray high-voltage generator 2 applies, to the X-ray tube 3, a tube current suitable for each of X-ray radiography and X-ray fluoroscopy, and applies, to the X-ray tube 3, a tube voltage suitable for each of X-ray radiography and X-ray fluoroscopy, under the control of the X-ray control circuitry 21. The X-ray high-voltage generator 2 may acquire information on the attitude of the supporter 5 directly from the supporter 5, or via the control circuitry 11, etc.

The X-ray control circuitry 21 is a processor relating to control of the X-ray tube 3. The X-ray control circuitry 21 receives X-ray irradiation conditions from the interface 10. The X-ray control circuitry 21 controls the X-ray tube 3 on the basis of the X-ray irradiation conditions. The X-ray irradiation conditions indicate a value of a tube voltage, a value of a tube current, an irradiation time, etc. in each time of X-ray irradiation, for example.

The X-ray control circuitry 21 may control the driver of the X-ray tube 3 on the basis of information indicating the attitude of the supporter 5. Specifically, the X-ray control circuitry 21 reads anode rotation control data corresponding to the attitude of the supporter 5 from a database stored in the storage circuitry 23. The X-ray control circuitry 21 controls an input signal to a driver that drives (rotates) the rotating anode of the X-ray tube 3 based on the anode rotation control data. The database stores a C-arm angle, anode rotation control data (a rotation frequency and a voltage waveform), operation sound data, and noise determination in association with each other. In the present embodiment, it is assumed that the "attitude of the supporter 5" is defined by an angle of the C-arm (C-arm angle); however, the configuration is not limited thereto.

The processing circuitry 22 includes a processor and a memory as hardware resources. The processing circuitry 22 reads a control program stored in the storage circuitry 23 in response to a start instruction that is input by an operator via the interface 10. The processing circuitry 22 executes various functions to reduce noise caused by the attitude of the supporter 5, which supports the X-ray tube 3, in accordance with the read control program.

Examples of the functions of the processing circuitry 22 include an attitude setting function 22a, a collection function 22b, a determination function 22c, an update function 22d, a parameter setting function 22e, and an acquisition function 22f, etc. The attitude setting function 22a, the collection function 22b, the determination function 22c, the update function 22d, and the parameter setting function 22e are executed when a database is constructed for reducing noise caused by the attitude of the supporter 5, which supports the X-ray tube 3, and the acquisition function 22f is executed in actual use of the X-ray diagnostic apparatus 1.

The attitude setting function 22a sets the attitude of the supporter 5. Specifically, the attitude setting function 22a reads the C-arm angle stored in the database, and outputs the information on the read C-arm angle to the X-ray control circuitry 21. Alternatively, the attitude setting function 22a outputs the information on the read C-arm angle to the control circuitry 11.

The collection function 22b collects operation sounds at the time of anode boosting in the X-ray tube 3. Specifically, the collection function 22b starts collecting operation sound data based on an instruction to start boosting from the X-ray control circuitry 21, for example, and collects the operation sound data in a period (boosting period) during which the X-ray tube 3 is boosted. The collection function 22b stores the collected operation sound data in the database in association with the angle set by the attitude setting function 22a. The collection function 22b may acquire vibration data, instead of the operation sound data.

The "boosting" as used herein refers to increasing the rotation frequency of the rotating anode of the X-ray tube 3 to a desired rotation frequency. The "boosting period" refers to a period of time from a point in time when the rotation frequency of the rotating anode is set to when the rotation frequency of the rotating anode is stabilized. Specifically, the "boosting period" corresponds to, for example, periods of time during which the rotation frequency of the rotating anode is increased from zero to 60 Hz (or 50 Hz), from zero to 180 Hz (or 150 Hz), and from 60 Hz (or 50 Hz) to 180 Hz (or 150 Hz).

The determination function 22c outputs a determination result by determining whether or not the operation sound data collected by the collection function 22b exceeds a threshold value. Specifically, the determination function 22c outputs "NG" (No Good) as a determination result if the operation sound data exceeds a threshold value, and outputs "OK" as the determination result if the operation sound data does not exceed the threshold value, for example. The determination method by the collection function 22b is not limited thereto, and "NG" may be output as the determination result if a certain threshold value is exceeded for a predetermined period of time. The collection function 22b may determine vibration data instead of the operation sound data.

The update function 22d updates a database of the storage circuitry 23 based on the determination result determined by the determination function 22c. Specifically, the update function 22d inputs "NG" to a noise determination column in the database if the determination result is "NG", and outputs "OK" to the noise determination column in the database if the determination result is "OK".

The parameter setting function 22e sets a parameter at the time of anode boosting. Specifically, the parameter setting function 22e sets, in the X-ray control circuitry 21, a rotation frequency different from a rotation frequency set by default as a parameter. Of the rotation frequencies that do not produce noise, it is desirable that the rotation frequency set by the parameter setting function 22e is close to a rotation frequency set by default. A parameter may be a voltage waveform, or may include both a rotation frequency and a voltage waveform.

The acquisition function 22f acquires an attitude of the supporter 5. The acquisition function 22f may acquire information indicating the attitude of the supporter 5 via the X-ray control circuitry 21, the control circuitry 11, or the like.

The processing circuitry 22 may determine whether or not noise has been measured with respect to all the attitudes stored in the database, and may determine whether or not "NG" is present in the noise determination by referring to the database in the storage circuitry 23.

The storage circuitry 23 stores a control program for reducing noise caused by the attitude of the supporter 5, which supports the X-ray tube 3. The storage circuitry 23 stores a database for controlling the anode rotation of the X-ray tube 3.

The X-ray tube 3 generates X-rays based on the tube current applied from the X-ray high-voltage generator 2 and the tube voltage applied from the X-ray high-voltage generator 2. The X-rays generated by the X-ray tube 3 are applied to a subject P. The X-ray tube 3 in the present embodiment corresponds to a rotating anode type X-ray tube.

The rotating anode of the X-ray tube 3 is driven based on a parameter received from the X-ray control circuitry 21. Specifically, rotation of the rotating anode of the X-ray tube 3 is controlled based on the rotation frequency included in the parameter. The rotation frequency used for driving (rotating) the rotating anode of the X-ray tube 3 is, for example, 60 Hz (or 50 Hz) in X-ray fluoroscopy, and 180 Hz (or 150 Hz) in X-ray radiography. However, the value of the rotation frequency is not limited thereto.

The rotation of the rotating anode of the X-ray tube may be controlled based on the voltage waveform included in the parameter. The voltage waveform is usually configured in such a manner that the torque is increased by sharpening the rise of the voltage (i.e., making the waveform close to a square wave). However, a square wave tends to produce sound more easily (i.e., generates noise easily) as the torque increases. Thus, in order to reduce the noise, the voltage waveform may be configured in such a manner that the rise of the voltage becomes gentle (e.g., as in a sign wave).

Figure 2:
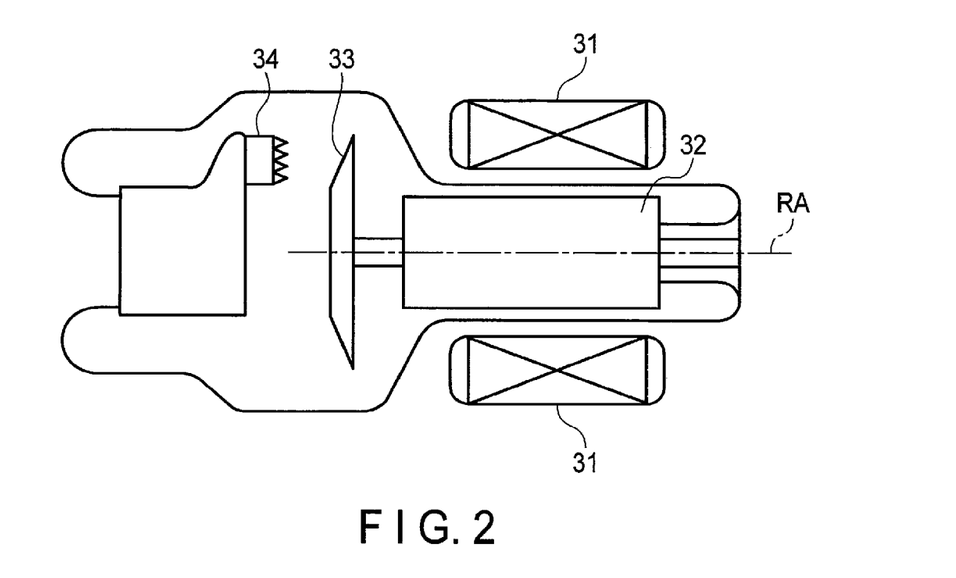
FIG. 2 is a diagram showing an example of a configuration of an X-ray tube device that includes an X-ray tube according to the embodiment.

FIG. 2 illustrates a part of a configuration of an X-ray tube device including the X-ray tube 3. The X-ray tube device includes: a driver including a stator 31 and a rotator 32; a target 33; and a filament 34. The X-ray tube 3 is usually configured of a rotator 32, a target 33, and a filament 34; however, the configuration includes a stator 31 as well, for convenience in explanation. That is, the "X-ray tube" in the present embodiment may include an element other than an X-ray tube in the configuration of the X-ray tube device.

The stator 31 receives a supply of a driving power via circuitry (not shown in the drawings) from the X-ray high-voltage generator 2. Upon receiving the supply of the driving power, the stator 31 generates a rotating magnetic field, and rotates the rotator 32. That is, the stator 31, together with the rotator 32, configures an induction motor (alternating-current motor).

The rotator 32 supports the target 33 on a rotational axis RA. The rotator 32 is rotated around the rotational axis RA by a rotating magnetic field generated by the stator 31. That is, the rotator 32 rotates the target 33 by its own rotation.

The target 33 is supported on the rotational axis RA of the rotator 32. The target 33 rotates around the rotational axis RA by the rotation of the rotator 32.

The filament 34 receives a supply of a filament current via a circuit (not shown in the drawings) from the X-ray high-voltage generator 2. The filament 34 is heated upon receiving the supply of the filament current, and emits thermoelectrons.

The X-ray detector 4 detects X-rays that have been generated from the X-ray tube 3 and have been transmitted through the subject P. The X-ray detector 4 includes, for example, a flat panel detector (FPD) capable of detecting X-rays. The FPD includes a plurality of semiconductor detection elements. The types of semiconductor detection elements include an indirect conversion type and a direct conversion type. In the indirect conversion type, incident X-rays are converted into light by a scintillator such as a fluorescent substance, and the converted light is converted into electric signals. In the direct conversion type, incident X-rays are directly converted into electric signals. An image intensifier may be used as the X-ray detector 4.

The electric signals generated by a plurality of semiconductor detection elements in accordance with the incident X-rays are output to an analog-to-digital (A/D) converter (not shown in the drawings). The A/D converter converts the electric signals into digital data. The A/D converter outputs the digital data to the image generation circuitry 8.

The supporter 5 supports the X-ray tube 3 and the X-ray detector 4, which are placed opposite to each other, in an inclinable manner. Specifically, the supporter 5 corresponds to the C-arm. As the supporter 5, an Q-arm may be used instead of the C-arm. Moreover, the supporter 5 is not limited to a configuration including a C-arm or an Q-arm, and may be configured to include two arms (such as robot arms) that respectively and independently support the X-ray tube 3 and the X-ray detector 4. The supporter 5 is not limited to, for example, an over tube system or an under tube system, and may be applicable to any form.

Figure 3:
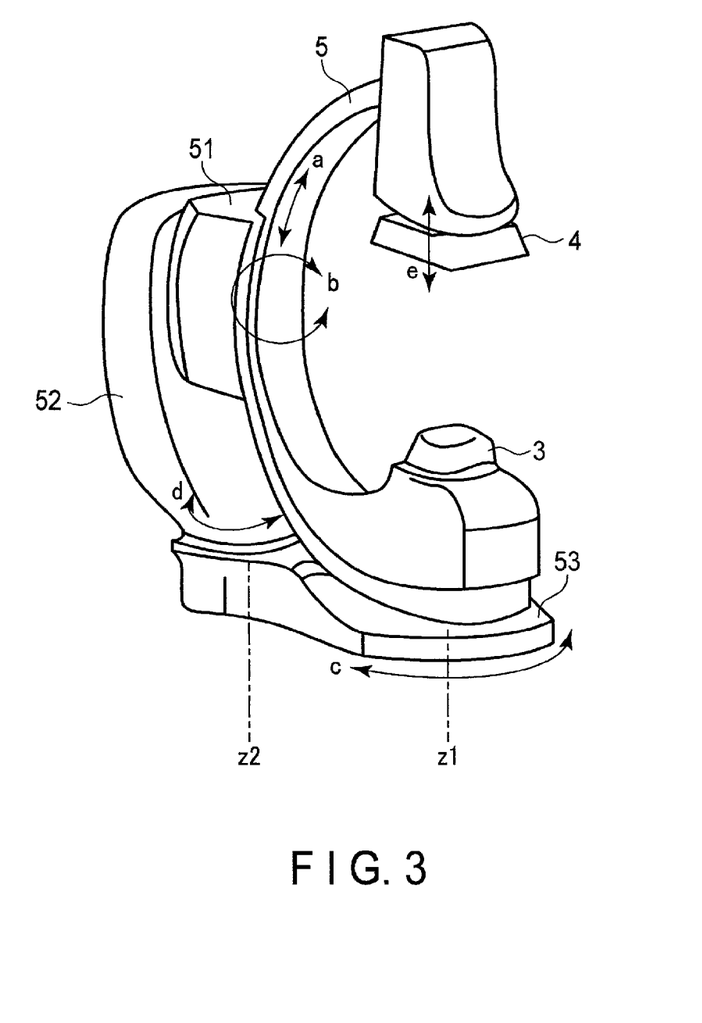
FIG. 3 is a diagram showing an outer appearance of a C-arm device according to the embodiment.

FIG. 3 illustrates an outer appearance of the C-arm device. In the C-arm device shown in FIG. 3, a C-arm that includes the X-ray tube 3 and the X-ray detector 4 mounted on its ends is used as the supporter 5. The supporter 5 is supported by a stand 52 via a supporter holder 51. The supporter 5 is mounted on a side surface of the supporter holder 51 so as to be slidable in the directions of the arrow a. The supporter holder 51 is mounted so as to be rotatable in the directions of the arrow b with respect to the stand 52. The X-ray detector 4 is mounted so as to be slidable in the imaging axis direction (in the directions of the arrow e) connecting the X-ray tube 3 and the X-ray detector 4.

One end of a floor-turnable arm 53 arranged on a floor surface (not shown in the drawings) is mounted so as to be rotatable around a rotation axis z1 (in the directions of the arrow c) vertical to the floor surface. The other end of the floor-turnable arm 53 is mounted in such a manner that the stand 52 is rotatable around a rotation axis z2 (in the directions of the arrow d) vertical to the floor surface.

Figure 4A:
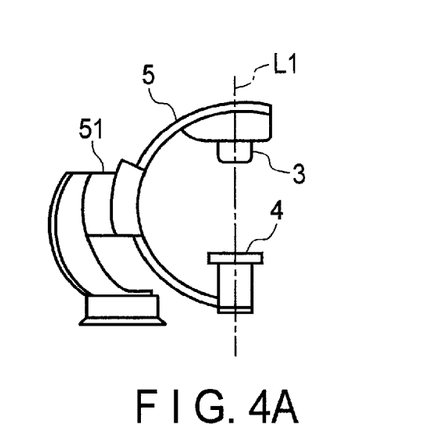
FIG. 4A is a diagram showing an example of a reference position of the C-arm device according to the embodiment.

FIG. 4A shows an example of a reference position of the C-arm device. FIG. 4A corresponds to a lateral view of the C-arm device shown in FIG. 3. Moreover, FIG. 4A corresponds to the state in which the stand 52 shown in FIG. 3 is rotated in a direction of the arrow c by 90 degrees, and the supporter holder 51 shown in FIG. 3 is rotated by 180 degrees in a direction of the arrow b. Therefore, FIG. 4A shows a state in which the C-arm is rotated to position the X-ray tube 3 above the X-ray detector 4. At this time, the imaging axis L1 that connects the X-ray tube 3 and the X-ray detector 4 is vertical to the floor surface.

Figure 4B:
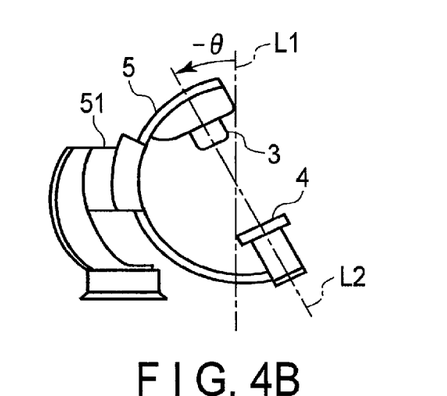
FIG. 4B is a diagram showing an example of an operation of the C-arm device according to the embodiment.

FIG. 4B shows an example in which the supporter 5 of the C-arm device is slid in a direction of the arrow a. Specifically, in FIG. 4B, the supporter 5 is slid in a direction that makes the X-ray tube 3 closer to the supporter holder 51, with reference to the C-arm device in the state shown in FIG. 4A. An imaging axis L2 that connects the X-ray tube 3 and the X-ray detector 4 after the sliding is inclined by an angle of $-\theta$ degrees with respect to the imaging axis L1.

Figure 4C:
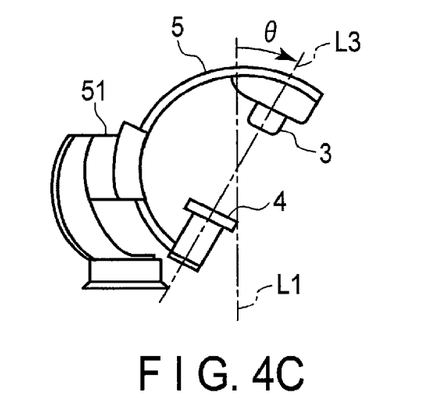
FIG. 4C is a diagram showing an example of an operation of the C-arm device according to the embodiment.

FIG. 4C shows an example in which the supporter 5 of the C-arm device is slid in another direction of the arrow a. Specifically, in FIG. 4C, the supporter 5 is slid in a direction that takes the X-ray tube 3 away from the supporter holder 51, with reference to the C-arm device in the state shown in FIG. 4A. An imaging axis L3 that connects the X-ray tube 3 and the X-ray detector 4 after the sliding is inclined by an angle of $\theta$ degrees with respect to the imaging axis L1.

In the present embodiment, the attitude of the supporter 5 that is slid in a direction of the arrow a will be described. Accordingly, it is assumed that the angle of the C-arm is set to, for example, seven-level angles A-G. Specifically, the angle A is set to $-\theta$, the angle D is set to zero, the angle G is set to $\theta$, the angles B and C are set to angles between $-\theta$ and zero, and the angles E and F are set to an angle between zero and $\theta$.

A bed (not shown in the drawings) includes a table top 6 (also referred to as a spine table) on which a subject P is placed. The subject P is placed on the table top 6.

A drive device (not shown in the drawings) drives each of the supporter 5 and the bed, for example, under the control of the control circuitry 11. During X-ray fluoroscopy and X-ray radiography, a subject P placed on the table top 6 is arranged between the X-ray tube 3 and the X-ray detector 4. Also, the drive device drives the X-ray tube 3 and the supporter 5, for example, under the control of the control circuitry 11. Furthermore, the drive device may rotate the X-ray detector 4 with respect to the X-ray tube 3, under the control of the control circuitry 11. The drive device may drive the X-ray tube 3 and the supporter 5 under the control of the X-ray control circuitry 21.

The measurement device 7 corresponds to, for example, a noise meter. The measurement device 7 measures, for example, an operation sound generated at the time of anode boosting in the X-ray tube 3 under the control of the X-ray control circuitry 21. In data (operation sound data) on the measured operation sound, the time and the recording level (dB), for example, are associated with each other. The measurement device 7 stores the operation sound data in the storage circuitry 23. The measurement device 7 may be a vibration meter (or an acceleration meter), and may measure vibrations generated at the time of anode boosting in the X-ray tube 3. That is, the measurement device 7 may be in any form that is capable of measuring an event relating directly or indirectly to an operation sound.

The image generation circuitry 8 generates an X-ray image, based on digital data output from the X-ray detector 4 via the A/D converter. The image generation circuitry 8 outputs the generated X-ray image to the storage circuitry 12, an external storage device (not shown in the drawings), etc.

The communication interface 9 is circuitry relating to, for example, a network, and an external storage device (not shown in the drawings). An X-ray image, etc. obtained by the X-ray diagnostic apparatus 1 can be transferred to other devices via the communication interface 9 and a network.

The interface 10 receives various instructions and information inputs from an operator. The interface 10, which is connected to the control circuitry 11, converts an input operation received from the operator into an electric signal, and outputs the electric signal to the control circuitry 11. The interface 10 corresponds to, for example, a pointing device such as a mouse, or an input device such as a keyboard. The interface 10 is not limited to a physically-operated component such as a mouse, and a keyboard. Examples of the interface 10 include a case where an electric signal corresponding to an input operation is received from an external input device provided separately from the X-ray diagnostic apparatus 1 and the received electric signal is output to various circuits. The interface 10 may be referred to as an input interface.

The control circuitry 11 is a processor that controls various elements, various circuits, a drive device, etc. in the X-ray diagnostic apparatus 1. The control circuitry 11 temporarily stores, in a memory (not shown in the drawings), information such as the operator's instructions, for example, sent from the interface 10. The control circuitry 11 controls the X-ray detector 4, the drive device, etc. to perform X-ray radiography and X-ray fluoroscopy in accordance with, for example, the operator's instructions stored in the memory. Furthermore, the control circuitry 11 controls, for example, the X-ray image generation processing in the image generation circuitry 8. Instead of the X-ray control circuitry 21, the control circuitry 11 may control the X-ray high-voltage generator 2 upon receiving X-ray irradiation conditions from the interface 10, and may execute various functions of the processing circuitry 22.

The storage circuitry 12 stores a data constellation of various types of data, such as various X-ray images generated by the image generation circuitry 8, a system control program of the X-ray diagnostic apparatus 1, a diagnosis protocol executed in the control circuitry 11, the operator's instructions transmitted from the interface 10, radiographic conditions regarding X-ray radiography and fluoroscopic conditions regarding X-ray fluoroscopy; error information; and various types of data received via the network.

The storage circuitry 12 is configured of a memory for recording electric information, such as a hard disk drive (HDD), and peripheral circuitry such as a memory controller and a memory interface accompanied by the memory. Such a memory is not limited to a HDD, and a solid state drive (SSD), a magnetic disk (e.g., a floppy (registered trademark) disk and a hard disk), an optical disk (e.g., a CD, a DVD, and a Blu-ray (registered trademark)), a semiconductor memory, etc. can be suitably used.

The display 13 displays an X-ray image generated by the image generation circuitry 8 under the control of the control circuitry 11. The display 13 is a display device such as a CRT display, a liquid crystal display, an organic EL display, an LED display, a plasma display, or any other display or monitor known in this technical field.

Operations of Database Construction

Next, operations of the X-ray diagnostic apparatus 1 configured as above will be explained using the flowchart shown in FIG. 5 and the database shown in FIG. 6. An explanation will be given mainly of the operations of constructing a database for reducing noise caused by the attitude of the supporter 5 that supports the X-ray tube 3. In the database shown in FIG. 6, the C-arm angle, the anode rotation control data (rotation frequency and voltage waveform), the operation sound data, and the noise determination are stored in association with each other.

First, a measurement device 7 is mounted at the time of installation (or an inspection) before the X-ray diagnostic apparatus 1 is used. When a program for measuring operation sounds relating to the X-ray tube 3 is selected by an instruction from the operator, the X-ray diagnostic apparatus 1 starts execution of the program, thereby starting step ST11.

In step ST11, the attitude setting function 22a sets the supporter 5 to a desired attitude. In the present embodiment, it is assumed that the attitude is one of the cases where the C-arm is slid in one direction, as shown in FIGS. 4A-C. Specifically, the attitude setting function 22a sets the angle of the C-arm to a predetermined value. The attitude is not limited to the above-described one, and may be any attitude that the C-arm device may take.

After the angle of the C-arm is set to a predetermined value, the processing circuitry 22 instructs the X-ray control circuitry 21 to rotate the anode of the X-ray tube 3 at a high speed (boost the anode). The parameters that boost the anode are, for example, a rotation frequency and a voltage waveform.

In step ST12, the collection function 22b collects operation sounds at the time of anode boosting in the X-ray tube 3. Specifically, the collection function 22b starts collecting operation sound data based on an instruction to start boosting from the X-ray control circuitry 21, and collects the operation sound data during the period in which the X-ray tube 3 is boosted. The collection function 22b stores the collected operation sound data in the storage circuitry 23, in association with the angle set in step ST11.

In step ST13, the determination function 22c determines whether or not the operation sound data collected in step ST12 exceeds a threshold value. If the operation sound data does not exceed the threshold value, the processing advances to step ST14, and if the operation sound data exceeds the threshold value, the processing advances to step ST15.

In step ST14, the update function 22d inputs "OK" to the noise determination column in the database of the storage circuitry 23.

In step ST15, the update function 22d inputs "NG" to the noise determination column in the database of the storage circuitry 23.

In step ST16, the processing circuitry 22 determines whether or not the operation sound measurement has been performed with respect to all the attitudes. If the operation sound measurement has been performed with respect to all the attitudes, the processing advances to step ST17. If the operation sound measurement has not been performed with respect to all the attitudes, the attitude setting function 22a sets the supporter 5 to a different attitude, and the processing returns to step ST12.

In step ST17, the processing circuitry 22 refers to the database in the storage circuitry 23, and determines whether or not "NG" is present in the noise determination. If "NG" is present in the noise determination, the processing advances to step ST18. If "NG" is not present in the noise determination, the processing is ended.

The above-described flow from step ST11 to step ST15 will be explained with reference to the database shown in FIG. 6. The attitude setting function 22a sets the supporter 5 to the C-arm angle B. Subsequently, the processing circuitry 22 instructs the rotation frequency f_1 and the voltage waveform v_1 corresponding to the C-arm angle B to the X-ray control circuitry 21. The collection function 22b collects the operation sound data S_B at the time of anode boosting in the state of the C-arm angle B, the rotation frequency f_1, and the voltage waveform v_1. The determination function 22c determines that the operation sound data S_B exceeds a threshold value, and the update function 22d inputs "NG" as the noise determination. In the case of the C-arm angle G, similar operations are performed until "NG" is input as the noise determination.

Figure 5:
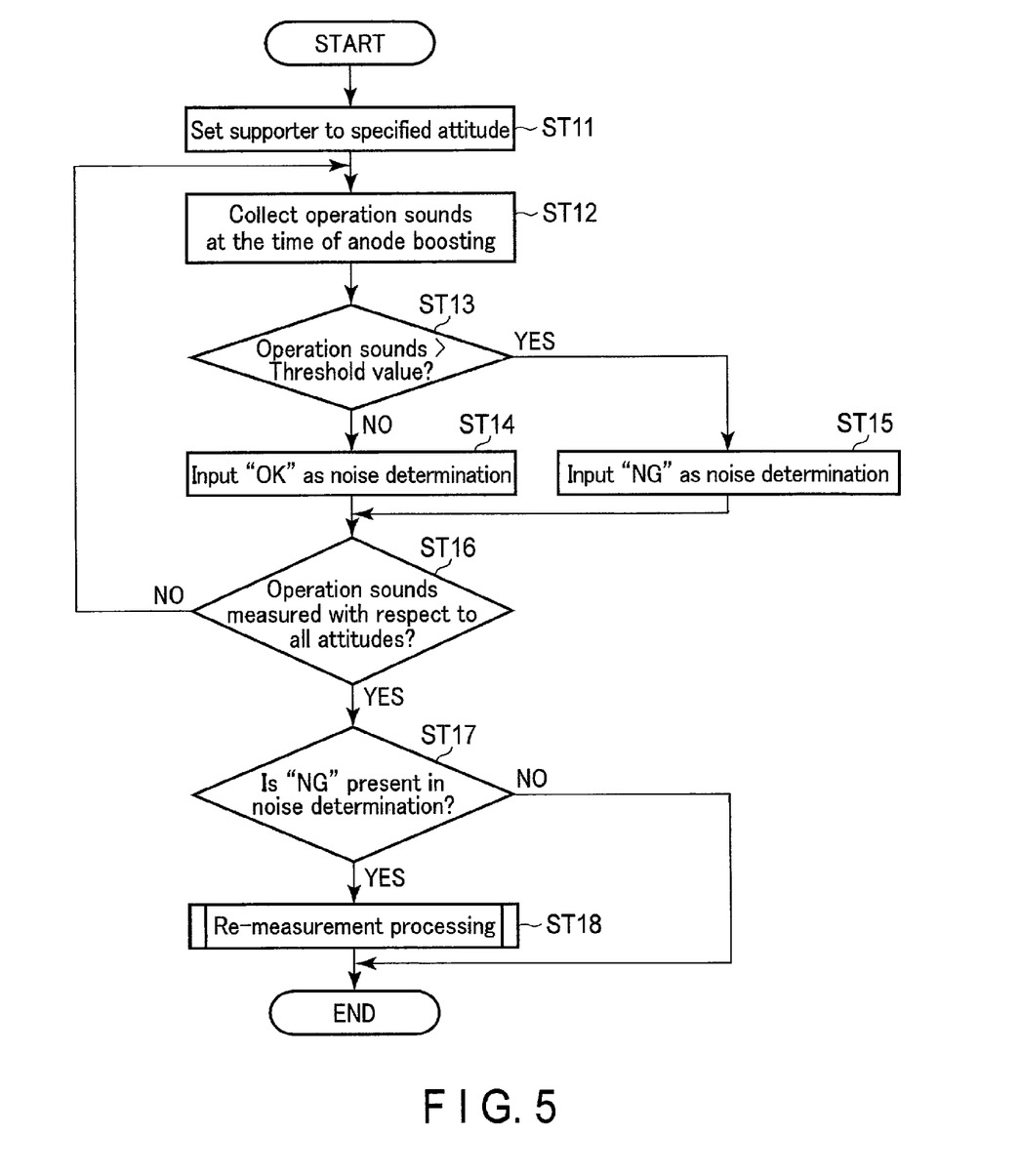
FIG. 5 is a flowchart illustrating an operation according to the embodiment.
Figure 6:
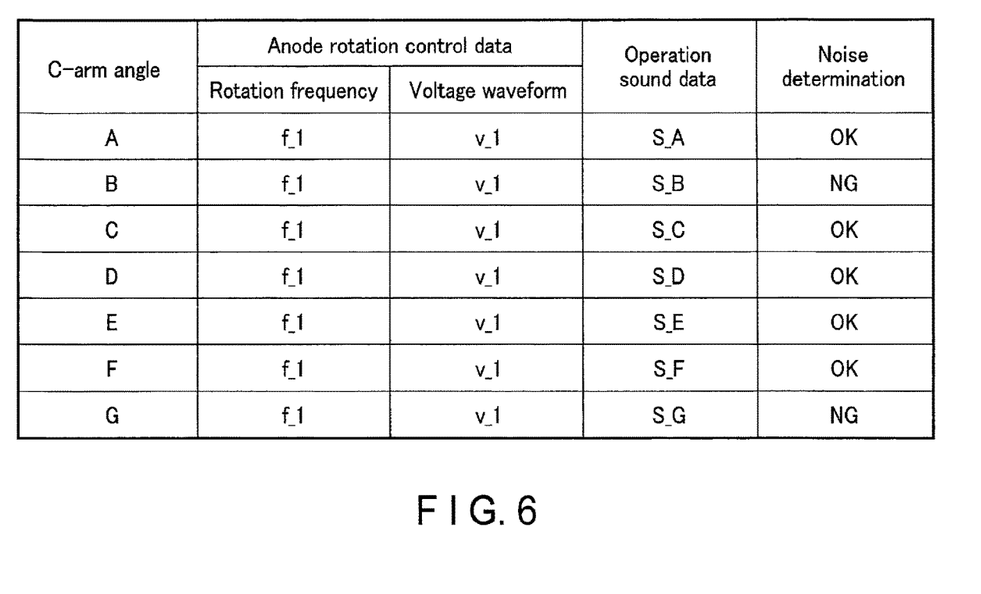
FIG. 6 is a diagram showing an example of a database according to the embodiment.
Figure 7:
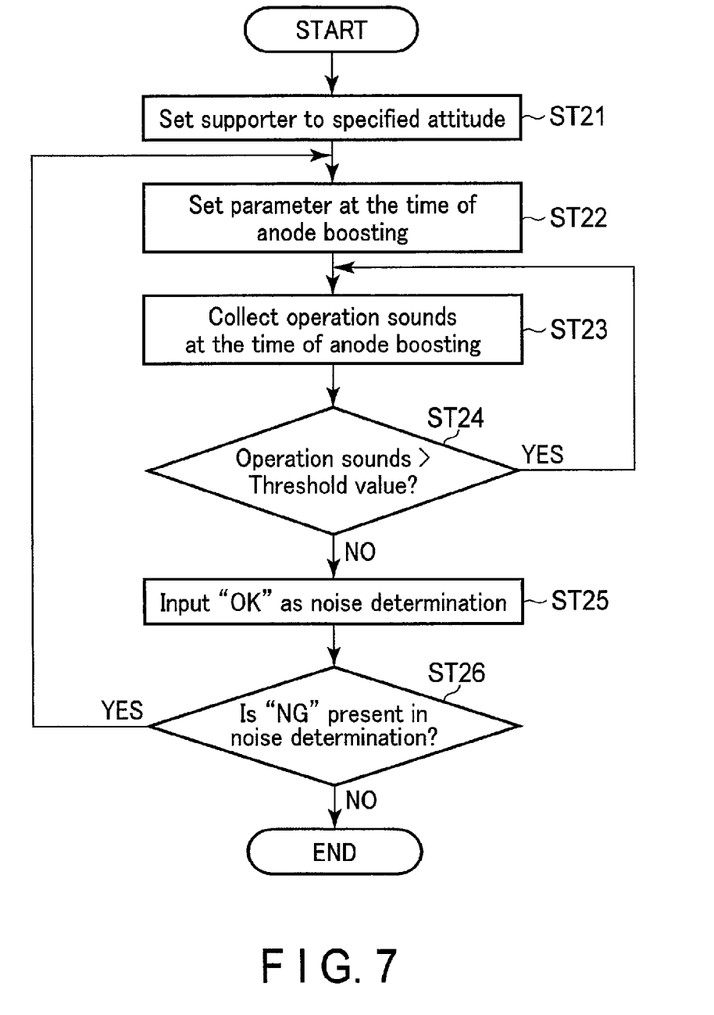
FIG. 7 is a flowchart illustrating an operation of re-measurement processing shown in FIG. 5.

FIG. 7 illustrates a flowchart of re-measurement processing shown in step ST18 of FIG. 5.

In step ST21, the attitude setting function 22a sets the supporter 5 to a specified attitude. Specifically, the attitude setting function 22a sets the angle of the C-arm to an angle at which "NG" is input to the noise determination in the database of the storage circuitry 23.

In step ST22, the parameter setting function 22e sets a parameter to be used at the time of anode boosting. Specifically, the parameter setting function 22e sets, in the X-ray control circuitry 21, a rotation frequency different from a rotation frequency set by default as a parameter.

In step ST23, the collection function 22b collects operation sounds at the time of anode boosting in the X-ray tube 3. The collection function 22b stores, in the storage circuitry 23, the collected operation sound data in association with the angle set in step ST21.

In step ST24, the determination function 22c determines whether or not the operation sound data collected in step ST23 exceeds a threshold value. If the operation sound data does not exceed the threshold value, the processing advances to step ST25. If the operation sound data exceeds the threshold value, the parameter setting function 22e sets the parameter to be used at the time of anode boosting to a different value, and the processing returns to step ST23.

In step ST25, the update function 22d inputs "OK" as the noise determination in the database of the storage circuitry 23.

In step ST26, the processing circuitry 22 determines whether or not "NG" is present in the noise determination in the database of the storage circuitry 23. If "NG" is present in the noise determination, the attitude setting function 22a sets the supporter 5 to a different attitude, and the processing returns to step ST22. If "NG" is not present in the noise determination, the processing is ended.

The flow from step ST21 to step ST25 will be explained using the database shown in FIG. 8. At the point in time when the processing advances to step ST21, if "NG" is input to the noise determination, the C-arm angle is set to either "B" or "G" (see FIG. 6). First, the attitude setting function 22a sets the supporter 5 to a C-arm angle B. Subsequently, the parameter setting function 22e changes the rotation frequency corresponding to the C-arm angle B from f_1 to f_2, and instructs the X-ray control circuitry 21 of the change. The collection function 22b collects the operation sound data S_B' at the time of anode boosting in the state of the C-arm angle B, the rotation frequency f_2, and the voltage waveform v_1. The determination function 22c determines that the operation sound data S_B' is less than a threshold value, and the update function 22d inputs "OK" as the noise determination.

Next, the attitude setting function 22a sets the supporter 5 to a C-arm angle G. Subsequently, the parameter setting function 22e changes the rotation frequency corresponding to the C-arm angle G from f_1 to f_3, and instructs the X-ray control circuitry 21 of the change. The collection function 22b collects the operation sound data S_G' at the time of anode boosting in the state of the C-arm angle G, the rotation frequency f_3, and the voltage waveform v_1 (not shown in the drawings). The determination function 22c determines that the operation sound data S_G' has exceeded a threshold value. The processing returns, and the parameter setting function 22e changes the voltage waveform corresponding to the C-arm angle G from v_1 to v_2, and instructs the X-ray control circuitry 21 of the change. The collection function 22b collects operation sound data S_G" at the time of anode boosting in the state of the C-arm angle G, the rotation frequency f_3, and the voltage waveform v_2. The determination function 22c determines that the operation sound data S_G" is less than a threshold value, and the update function 22d inputs "OK" as the noise determination.

In the present embodiment, step ST15 may be replaced with the re-measurement processing in step ST18. In this case, the processing skips step ST26, advances to step ST16 after step ST25, further skips step ST17, and is ended in the case of "YES" in step ST16.

(Operations in Actual Use)

Figure 9:
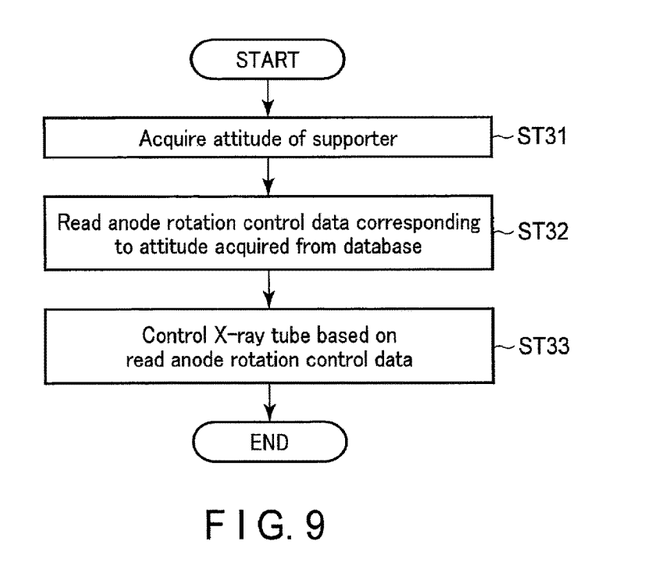
FIG. 9 is a flowchart illustrating a control operation of an X-ray tube according to the embodiment.

Next, operations of the X-ray diagnostic apparatus 1 using the database configured by the aforementioned processing shown in FIGS. 5 and 7 will be explained using the flowchart shown in FIG. 9. A description will be given mainly of the operations of the X-ray diagnostic apparatus 1 in actual use.

First, a subject P is placed on the table top 6 of the bed. In the X-ray diagnostic apparatus 1, a preset examination type and a preset examination name are selected by an operation by an operator, and imaging conditions (X-ray conditions) associated with the selected examination type and examination name are set. Subsequently, the X-ray diagnostic apparatus 1 sets an attitude of the supporter 5 by an operation by the operator, starts X-ray radiography (X-ray fluoroscopy) by turning on an imaging switch (or an irradiation switch) of the interface 10 by a further operation by the operator, and starts step ST31.

In step ST31, the acquisition function 22f acquires the attitude of the supporter 5.

In step ST32, the X-ray control circuitry 21 reads anode rotation control data corresponding to the attitude acquired in step ST31 from the database stored in the storage circuitry 23.

In step ST33, the X-ray control circuitry 21 controls the X-ray tube 3 on the basis of the anode rotation control data read in step ST31.

Figure 8:
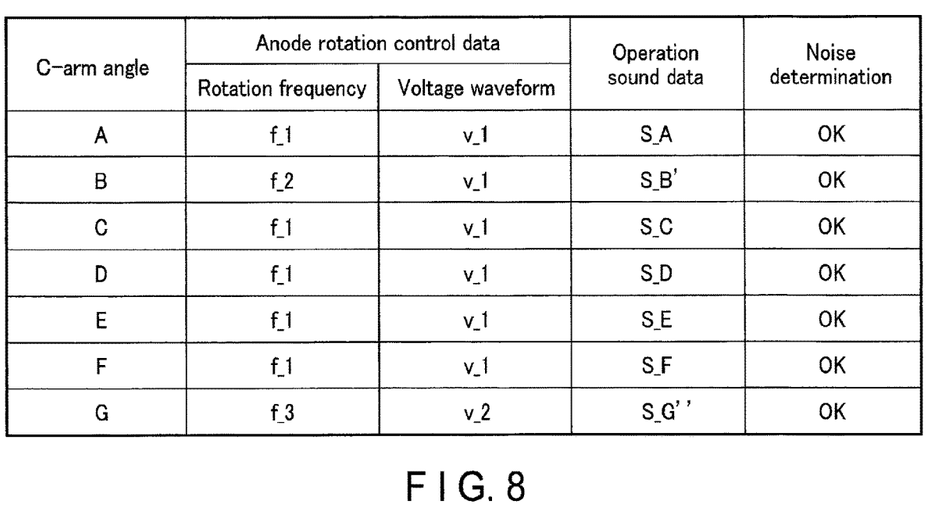
FIG. 8 is a diagram showing an example of a database according to the embodiment.

As a specific example, if the attitude of the supporter 5 acquired by the acquisition function 22f matches the C-arm angle G in FIG. 8, the X-ray control circuitry 21 reads the rotation frequency f_3 and the voltage waveform v_2 as the anode rotation control data. The X-ray control circuitry 21 controls an input signal to the driver that drives the rotating anode of the X-ray tube 3 on the basis of the rotation frequency f_3 and the voltage waveform v_2.

(Another Configuration Example of Apparatus)

Figure 10:
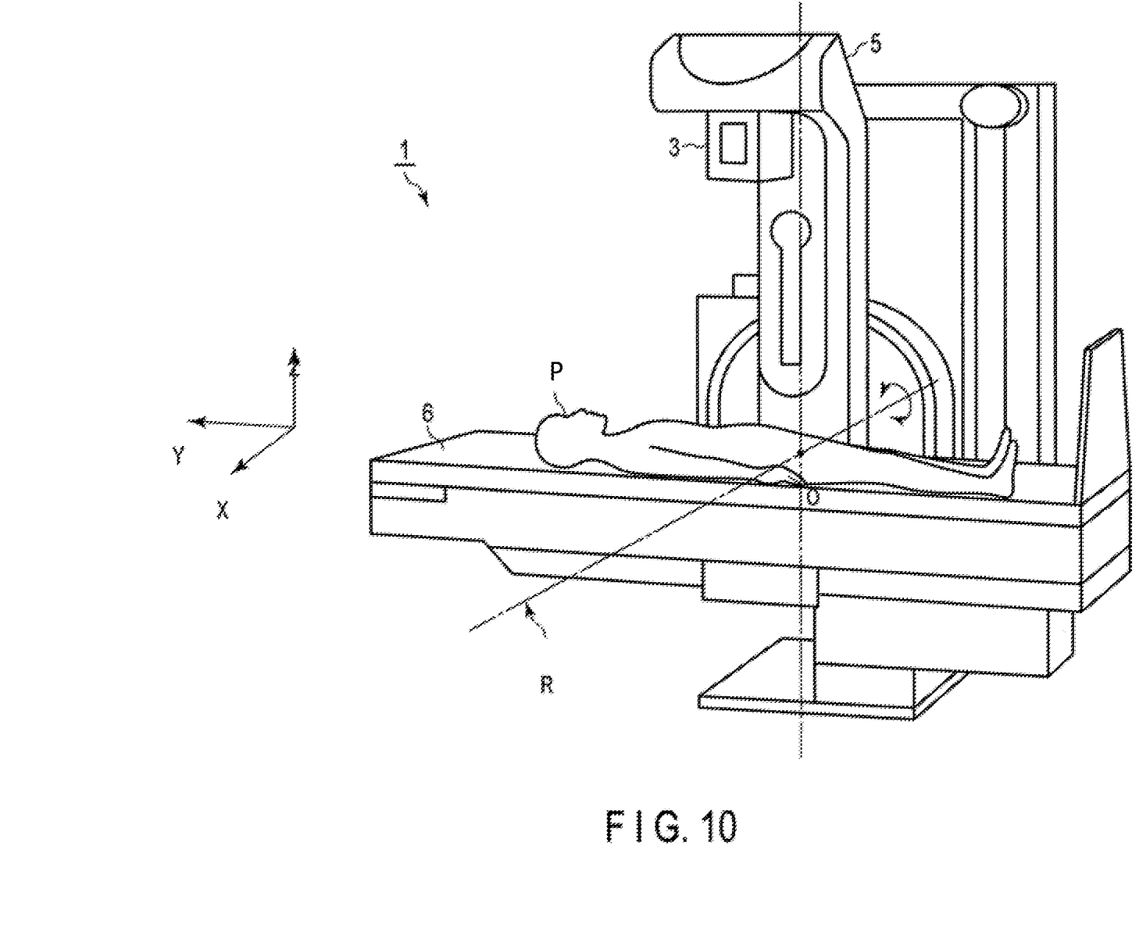
FIG. 10 is a diagram showing an outer appearance of an X-ray diagnostic apparatus that includes another supporter according to the embodiment.

FIG. 10 shows an outer appearance of an X-ray diagnostic apparatus 1 in which a supporter 5 that supports an X-ray tube 3 is integrally formed with a bed that includes a table top 6. FIG. 10 corresponds to an X-ray fluoroscopic diagnosis apparatus typically used in gastrointestinal series examinations, etc. In FIG. 10, a direction that passes through an effective focal spot of the X-ray tube 3 and that is vertical to a detection surface of an X-ray detector 4 (not shown) arranged below the table top 6 is defined as a z-axis, a direction that is along the long side of the table top 6 and that is vertical to the z-axis is defined as a y-axis, and a direction that is parallel to the z-axis and the y-axis (along the short side of the table top 6) is defined as an x-axis.

The X-ray tube 3 is supported on one end of the supporter 5. The supporter 5 supports the X-ray tube 3 on one end, and the other end is supported by the bed. The bed supports the supporter 5. The supporter 5 rotates around a rotational axis R in the x axis direction, which passes through a fulcrum O. At this time, the "attitude of the supporter 5" is defined by the angle by which the supporter 5 including the table top 6 rotates around the rotational axis R. The angle of the supporter 5 is determined in accordance with the inclination of the table top 6, with reference to the state of the table top 6 that is parallel to the floor surface, which is set as zero degrees.

As explained above, according to an embodiment, an X-ray diagnostic apparatus acquires information indicating an attitude of a supporter that supports an X-ray tube in an inclinable manner, and controls a driver that rotates a rotating anode of the X-ray tube on the basis of information indicating the acquired attitude. Thus, by controlling the rotating anode in accordance with the attitude of the supporter, the X-ray diagnostic apparatus is capable of preventing noise from occurring in advance, thus reducing noise, regardless of the attitude of the supporter that supports the rotating anode type X-ray tube.

Since noise can be reduced during an examination and a treatment, the operator of the X-ray diagnostic apparatus feels reduced stress from the noise, and the patient feels reduced discomfort from the noise.

According to the embodiment, since the X-ray diagnostic apparatus is capable of controlling a driver based on a rotation frequency associated with the attitude of the supporter, it is possible to prevent a match between the rotation frequency of the rotating anode and the resonance frequency of the supporter, thereby preventing the occurrence of noise caused by resonance.

According to the embodiment, since the X-ray diagnostic apparatus is capable of controlling a driver based on a rotation frequency and a voltage waveform associated with the attitude of the supporter, it is possible to prevent a match between the rotation frequency of the rotating anode and the resonance frequency of the supporter, thereby preventing the occurrence of noise caused by resonance and reducing noise caused by the voltage waveform.

According to the embodiment, since the X-ray diagnostic apparatus is capable of storing the attitude of the supporter in association with a parameter relating to a control of a driver, it is possible to reduce noise, regardless of the attitude of the supporter that supports the rotating anode type X-ray tube.

According to the embodiment, an X-ray diagnostic apparatus sets an attitude of a supporter that supports an X-ray tube in an inclinable manner, and stores the set attitude in association with a parameter used to control a driver. The X-ray diagnostic apparatus collects sounds generated at the time of anode boosting of the X-ray tube in the set attitude, and stores information indicating whether or not a result of the collection exceeds a threshold value, in association with the set attitude. The X-ray diagnostic apparatus change the parameter stored in a memory based on whether or not the sounds exceed the threshold value, and stores the attitude and the changed parameter in association with each other. Furthermore, the X-ray diagnostic apparatus stores the set desired attitude and the set parameter in association with each other. Accordingly, the X-ray diagnostic apparatus is capable of preventing the occurrence of noise in advance, by setting a parameter for controlling the rotating anode in accordance with the attitude of the supporter, thereby reducing noise, regardless of the attitude of the supporter that supports the rotating anode type X-ray tube. In addition, by periodically recollecting data through maintenance, inspection, etc., and updating the database (control table), it is possible to reduce the noise while adapting to changes in resonance points with the passage of time.

According to the embodiment, since the X-ray diagnostic apparatus uses a rotation frequency as a parameter, it is possible to prevent a match between the rotation frequency of the rotating anode and the resonance frequency of the supporter, thereby preventing the occurrence of noise caused by resonance.

According to the embodiment, since the X-ray diagnostic apparatus uses a rotation frequency and a voltage waveform as parameters, it is possible to prevent a match between the rotation frequency of the rotating anode and the resonance frequency of the supporter, thereby preventing the occurrence of noise caused by resonance, and reducing noise caused by the voltage waveform.

According to the embodiment, the above-described configuration may be implemented by an X-ray high-voltage generator. For example, an X-ray high-voltage generator for an X-ray diagnostic apparatus, which includes an X-ray tube with a rotating anode, a driver that drives the rotating anode, and a supporter that supports the X-ray tube in an inclinable manner, acquires information indicating an attitude of a supporter, and controls the driver on the basis of information indicating the acquired attitude. Accordingly, the X-ray high-voltage generator is capable of preventing the occurrence of noise in advance by controlling the rotating anode in accordance with the attitude of the supporter, thereby reducing noise regardless of the attitude of the supporter that supports the rotating anode type X-ray tube.

Another Embodiment

According to the above-described embodiment, the X-ray diagnostic apparatus controls the driver of the X-ray tube on the basis of information associated with the attitude. On the other hand, according to another embodiment, the X-ray diagnostic apparatus collects real-time operation sounds, and adds an operation to control the driver of the X-ray tube if the volume of the collected operation sounds exceeds a threshold value. Thereby, the X-ray diagnostic apparatus is capable of reducing noise that can occur in accordance with changes in attitude with the passage of time, during the course of the operation of inclining the supporter, for example.

Figure 11:
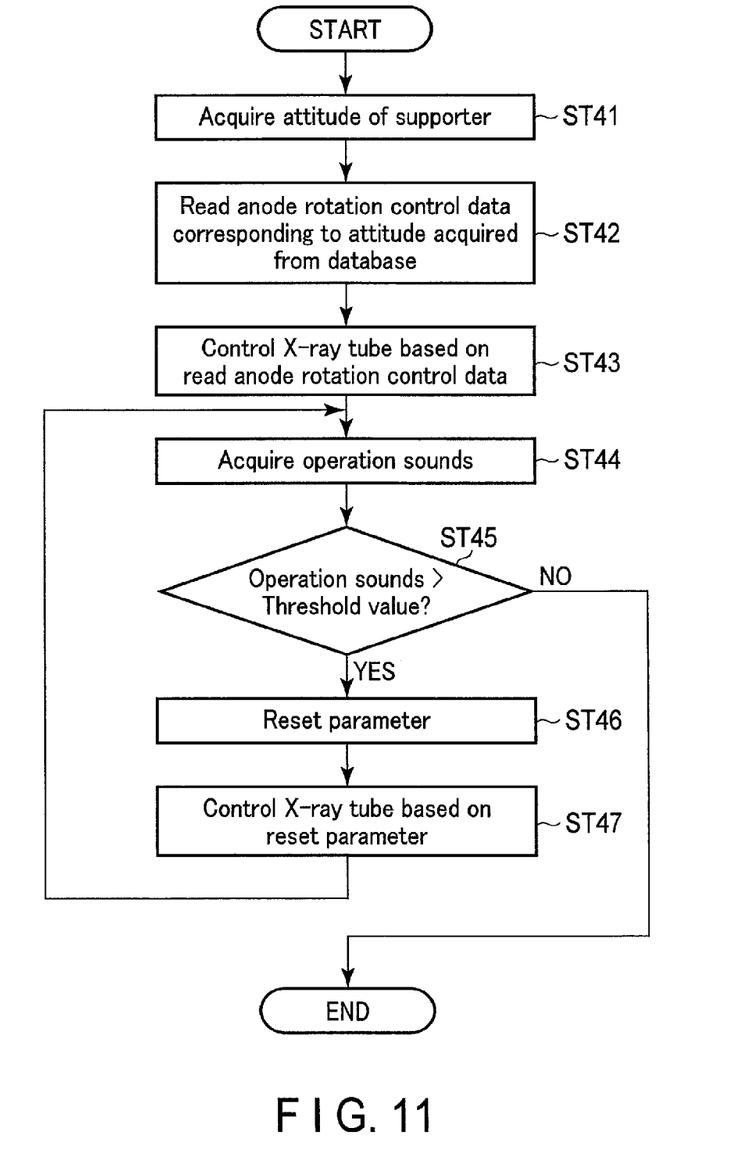
FIG. 11 is a flowchart illustrating an operation according to another embodiment.

In another embodiment, a parameter setting function 22e changes settings of the X-ray control circuitry 21 on the basis of the determination result output from the determination function 22c. Specifically, the parameter setting function 22e resets a parameter set in the X-ray control circuitry 21 on the basis of the determination result. The parameter setting function 22e changes the parameter if the determination result is "NG", and does not change the parameter if the determination result is "OK".

The X-ray control circuitry 21 controls the driver of the X-ray tube 3 on the basis of the changed parameter. The parameter setting function 22e may rewrite the value of the anode rotation control data in the database when the parameter is reset.

FIG. 11 is a flowchart illustrating an operation according to another embodiment. A description will be given mainly of the operations of the X-ray diagnostic apparatus 1 in actual use. Since preparations until the start of step ST41 are similar to the preparations until the start of step ST31, explanations thereof will be omitted. Also, since operations from step ST41 to step ST43 are similar to the operations from step ST31 to step ST33, explanations thereof will be omitted.

(Step ST44)

The collection function 22b collects the operation sounds of the X-ray tube 3.

(Step ST45)

The determination function 22c determines whether or not the operation sound data collected in step ST44 exceeds a threshold value. If the operation sound data exceeds the threshold value, the processing advances to step ST46. If the operation sound data does not exceed the threshold value, the processing is ended.

(Step ST46)

The parameter setting function 22e resets a parameter set in the X-ray control circuitry 21.

(Step ST47)

The X-ray control circuitry 21 controls the X-ray tube 3 on the basis of the parameter reset in step ST46. After the operation in step ST47, the processing returns to step ST44. That is, an operation sound after resetting of the parameter is determined, and the processing from step ST44 to step ST47 is repeatedly performed until the operation sound falls below the threshold value. On the other hand, if the operation sound falls below the threshold value in step ST45, the processing is ended.

(Modification)

In the previous another embodiment, the X-ray diagnostic apparatus controls the driver of the X-ray tube by automatically determining the operation sound. On the other hand, in a modification, the X-ray diagnostic apparatus may reset the parameter upon receiving the operator's instruction. Thereby, the X-ray diagnostic apparatus is capable of resetting the parameter according to, for example, the individual operator's (or subject's) feeling.

According to the modification, the acquisition function 22f acquires the operator's instruction given via the interface 10. The operator's instruction corresponds to, for example, information relating to a change in parameters. The operator gives an instruction to cause the interface 10 to change the parameters of the X-ray control circuitry 21 upon perceiving the occurrence of noise, for example.

The term "processor" used in the above explanation refers to, for example, a central processing unit (CPU), a graphics processing unit (GPU), or circuitry such as an application-specific integrated circuit (ASIC) and a programmable logic device (e.g., a simple programmable logic device (SPLD), a complex programmable logic device (CPLD), and a field-programmable gate array (FPGA)).

The processor implements various functions by reading and executing programs stored in the storage circuitry. Instead of storing the programs in the storage circuitry, the programs may be directly integrated into the circuitry of the processor. In this case, the processor reads and executes the programs incorporated into the circuitry to implement various functions.

Each of the processors according to the present embodiment is not limited to a case where each processor is configured as a single circuit; a plurality of independent circuits may be combined into one processor to implement various functions thereof. In addition, a plurality of structural elements may be incorporated into one processor to implement the functions thereof.

The storage circuitry 12 according to the embodiment is an example of the memory as defined in the claims.

According to at least one of the above-described embodiments, it is possible to reduce noise, regardless of the attitude of the supporter that supports the rotating anode type X-ray tube.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. An X-ray diagnostic apparatus, comprising:
   an X-ray tube including a rotating anode;
   a driver that rotates the rotating anode;
   a supporter that supports the X-ray tube in an inclinable manner; and
   processing circuitry configured to:
   acquire information indicating an attitude of the supporter; and
   control the driver based on information indicating the acquired attitude.

2. The X-ray diagnostic apparatus according to claim 1, wherein
   the processing circuitry is further configured to:
   control the driver based on a rotation frequency associated with the acquired attitude.

3. The X-ray diagnostic apparatus according to claim 1, wherein
   the processing circuitry is further configured to:
   control the driver based on a voltage waveform associated with the acquired attitude.

4. The X-ray diagnostic apparatus according to claim 1, further comprising:
   a memory that stores the acquired attitude and a parameter relating to the control of the driver in association with each other.

5. The X-ray diagnostic apparatus according to claim 1, wherein
   the processing circuitry is further configured to:
   collect sounds generated from the X-ray tube; and
   determine whether or not a result of the collection exceeds a threshold value; and
   reset a parameter relating to the control of the driver based on a result of the determination.

6. The X-ray diagnostic apparatus according to claim 5, further comprising:
   a memory that stores the acquired attitude and the reset parameter in association with each other.

7. The X-ray diagnostic apparatus according to claim 1, wherein the processing circuitry is further configured to reset a parameter relating to the control of the driver in response to an operation by a user.

8. An X-ray diagnostic apparatus, comprising:
an X-ray tube including a rotating anode;
a driver that rotates the rotating anode;
a supporter that supports the X-ray tube in an inclinable manner; and
processing circuitry configured to:
set an attitude of the supporter; and
a memory that stores the set attitude of the supporter in association with a parameter used to control the driver.

9. The X-ray diagnostic apparatus according to claim 8, wherein
the processing circuitry is further configured to:
collect sounds generated at the time of anode boosting of the X-ray tube in the set attitude, and
the memory stores information indicating whether or not a result of the collection exceeds a threshold value, in association with the set attitude.

10. The X-ray diagnostic apparatus according to claim 9, wherein
the processing circuitry is further configured to:
change the parameter stored in the memory based on whether or not a result of the collection exceeds a threshold value, and
the memory stores the attitude and the changed parameter in association with each other.

11. The X-ray diagnostic apparatus according to claim 8, wherein
the parameter includes a rotation frequency.

12. The X-ray diagnostic apparatus according to claim 8, wherein
the parameter includes a voltage signal.

13. The X-ray diagnostic apparatus according to claim 8, wherein
the processing circuitry is further configured to:
acquire information indicating an attitude of the supporter; and
control the driver based on information indicating the acquired attitude and the parameter stored in the memory by referring to the memory.

14. An X-ray high-voltage generator for an X-ray diagnostic apparatus comprising
an X-ray tube with a rotating anode,
a driver that rotates the rotating anode, and
a supporter that supports the X-ray tube in an inclinable manner, the X-ray high-voltage generator comprising:
processing circuitry configured to:
acquire information indicating an attitude of the supporter; and
control the driver based on information indicating the acquired attitude.

15. The X-ray diagnostic apparatus according to claim 1, wherein the processing circuitry configured to control the driver based on the information indicating the acquired attitude is configured to control the driver based on a rotation frequency associated with the acquired attitude to avoid resonance in the supporter at the acquired attitude.

16. The X-ray diagnostic apparatus according to claim 8, wherein the parameter used to control the driver comprises a parameter to avoid resonance in the supporter at the attitude of the supporter.

17. The X-ray high-voltage generator according to claim 14, wherein the processing circuitry configured to control the driver based on the information indicating the acquired attitude is configured to control the driver based on a rotation frequency associated with the acquired attitude to avoid resonance in the supporter at the acquired attitude.

* * * * *